(12) United States Patent
Kirchner et al.

(10) Patent No.: US 10,294,337 B2
(45) Date of Patent: May 21, 2019

(54) PROCESS FOR PREPARING POLY(GLYCOLIDE-CO-LACTIDE) COPOLYMER MICROPARTICLES

(71) Applicant: Evonik Röhm GmbH, Darmstadt (DE)

(72) Inventors: Andreas Kirchner, Andernach (DE); Rosario Lizio, Dieburg (DE); Markus Rolf Rossmeissl, Darmstadt (DE); Wolfgang Luley, Griesheim (DE); Johannes Vorholz, Alzenau (DE); Silko Grimm, Rossdorf (DE); Marc Schneider, Saarbruecken (DE)

(73) Assignee: Evonik Röhm GmbH, Darmstadt (DE)

( * ) Notice: Subject to any disclaimer, the term of this patent is extended or adjusted under 35 U.S.C. 154(b) by 0 days.

(21) Appl. No.: 15/741,995

(22) PCT Filed: Jun. 21, 2016

(86) PCT No.: PCT/EP2016/064270
§ 371 (c)(1),
(2) Date: Jan. 4, 2018

(87) PCT Pub. No.: WO2017/005483
PCT Pub. Date: Jan. 12, 2017

(65) Prior Publication Data
US 2018/0201738 A1 Jul. 19, 2018

(30) Foreign Application Priority Data

Jul. 9, 2015 (EP) .................................. 15176023

(51) Int. Cl.
*A61K 9/14* (2006.01)
*C08J 3/09* (2006.01)
(Continued)

(52) U.S. Cl.
CPC ................. *C08J 3/12* (2013.01); *A61K 9/146* (2013.01); *A61K 47/34* (2013.01); *C08G 63/88* (2013.01); *C08J 3/095* (2013.01); *C08J 2367/04* (2013.01)

(58) Field of Classification Search
CPC ........ A61K 47/34; A61K 9/146; C08G 63/88; C08J 2367/04; C08J 3/095; C08J 3/12
See application file for complete search history.

(56) References Cited

U.S. PATENT DOCUMENTS

| | | | |
|---|---|---|---|
| 9,790,331 B2 | 10/2017 | Baer et al. | |
| 2012/0052120 A1* | 3/2012 | Castor .................. | A61K 9/4858 424/451 |
| 2016/0208057 A1 | 7/2016 | Baer et al. | |

OTHER PUBLICATIONS

Campardelli et al., "Solvent elimination from polymer nanoparticle suspensions by continuous supercritical extraction," J. of Supercritical Fluids 70 (2012) 100-105. (Year: 2012).*

(Continued)

*Primary Examiner* — Aradhana Sasan
(74) *Attorney, Agent, or Firm* — Grüneberg and Myers PLLC

(57) ABSTRACT

A process for preparing poly(lactide-co-glycolide) copolymer particles with an average particle size in the range of 50-800 nm includes transferring a mixture of poly(lactide-co-glycolide) copolymer, ethanol and carbon dioxide from a first reactor into a second reactor under rapid reduction of the pressure and expansion with phase separation into a gas phase, an ethanol aerosol and an ethanolic suspension containing poly(lactide-co-glycolide) copolymer particles, removing the carbon dioxide gas and the ethanol aerosol from the second reactor, and obtaining the poly(glycolide-co-lactide) copolymer particles in the form of an ethanolic suspension or in dry form from the second reactor.

16 Claims, 2 Drawing Sheets

(51) Int. Cl.
      *C08J 3/12*           (2006.01)
      *A61K 47/34*         (2017.01)
      *C08G 63/88*         (2006.01)

(56) References Cited

OTHER PUBLICATIONS

Jensen et al., "Spray drying of siRNA-containing PLGA nanoparticles intended for inhalation," Journal of Controlled Release 142 (2010) 138-145. (Year: 2010).*

Kongsombut et al.;"Formation of deagglomerated PLGA particles and PLGA-coated ultra fine powders by rapid expansion of supercritical solution with ethanol cosolvent"; Korean Journal of Chemical Engineering; vol. 24, No. 4; Jul. 1, 2008; pp. 838-845.

Conway et al.; "Poly(lactide-co-glycolide) Solution Behavior in Supercritical $CO_2$, $CHF_3$, and $CHClF_2$"; Journal of Applied Polymer Science; vol. 80; 2001; pp. 1155-1161.

Mishima et al.; "Microencapsulation of Proteins by Rapid Expansion of Supercritical Solution with a Nonsolvent"; AIChE Journal; vol. 46, No. 4; 2000; pp. 857-865.

International Search Report mailed in PCT/EP2016/064270 dated Oct. 13, 2016.

Written Opinion of the International Searching Authority.

* cited by examiner

PROCESS FOR PREPARING POLY(GLYCOLIDE-CO-LACTIDE) COPOLYMER MICROPARTICLES

FIELD OF THE INVENTION

The invention is concerned with a process for preparing poly(lactide-co-glycolide) copolymer particles.

TECHNICAL BACKGROUND

Conway et al. (J. of Appl. Polym. Sc., 80, 1155-1161, 2001) assumed that a high ratio of glycolide in a Poly(lactic-co-glycolid acid) copolymer (PLGA) may in general reduce its solubility in supercritical carbon dioxide.

Kongsombut et al. (Korean J. Chem. Eng., 25(4), 838-845 (2008) describes the formation of deagglomerated PLGA particles and PLGA-coated ultra-fine powders by rapid expansion of a supercritical carbon dioxide solution with ethanol as co-solvent. The PLGA polymer used was Poly (lactic-co-glycolic acid) with a PLA:PGA ratio of 85:15 and a Mw of 50.000-75.000. The PLGA was dissolved in supercritical carbon dioxide with ethanol as co-solvent in a stirred high-pressure reactor. Rapid expansion from that reactor took place through a nozzle which sprayed the solution onto a target plate or microgrid for analysis purposes. By this so-called RESS-process PLGA microparticles could be obtained which particle size could be controlled by the amount of the co-solvent ethanol added. Particle sizes ranged from about 50 to 500 nm. Furthermore ultra-fine powders from SiO2 or TiO2 were used as simulated core particles that could be coated with the PLGA in that process. The authors conclude that the RESS process with a co-solvent could be a promising enviromentally friendly technique for coating CO2-insoluble ultra-fine drug particles with a high molecular-weight polymer with limited solubility in CO2.

Mishima et al. (AlChE Journal, April 2000, vol. 46, No. 4, 857-865) described the microencapsulation of proteins by rapid expansion of a supercritical carbon dioxide solution with a non-solvent. Several polymers, among them a PLGA derivative, were dissolved in supercritical carbon dioxide with ethanol as co-solvent in a stirred high-pressure reactor. Rapid expansion from that reactor took place through a nozzle which sprayed the solution onto a target plate for analysis purposes. The PLGA polymer used was Poly(DL-lactic-co-glycolic acid) with an approximate weight fraction of glycolide of 50% and a Mw of 5.000. Particles consisting of a lysozyme or a lipase core coated with PLGA could be obtained by that so-called RESS process. The primary particle diameter of the coated particles was 22 μm with a standard deviation of around 1.65.

OBJECT AND SOLUTION

Poly(lactic-co-glycolic acid) (=PLGA) copolymers are known for a long time and are widely used in the biomedical field as biodegradable polymers for the controlled release of active pharmaceutically ingredients.

Usually PLGA is produced by a ring opening polymerization process of lactide and glycolide monomers. The polymerization products are however often in the form of a lump or nugget like polymer mass, which is often difficult to further process into a particle form. Thus there is a permanent need to provide processes which allow to gain PLGA polymers in the form of readily usable and well-defined particle sizes in acceptable yields. This aspect and further aspects of the invention are solved as claimed.

Kongsombut et al. (Korean J. Chem. Eng., 25(4), 838-845 (2008) described the formation of deagglomerated PLGA particles and PLGA-coated ultra-fine powders by rapid expansion of supercritical solution with ethanol. The PLGA polymer used was Poly(lactic-co-glycolic acid) with a PLA:PGA ratio of 85:15 and a Mw of 50.000-75.000. The PLGA was dissolved in supercritical carbon dioxide with ethanol as co-solvent in a stirred high-pressure reactor. Rapid expansion from that reactor took place through a nozzle which sprayed the solution onto a target plate or microgrid for analysis purposes only. Thus the process of Kongsombut et al. is a batch process of more scientific nature. No information of its applicability as an industrial process or its necessary modification to do so is given. Of similar academic nature is the teaching of Mishima et al. (AlChE Journal, April 2000, vol. 46, No. 4, 857-865). The PLGA polymer used by Mishima et al. was Poly(DL-lactic-co-glycolic acid) with an approximate weight fraction of glycolide of 50% and a Mw of 5.000.

Starting from Kongsombut et al. and Mishima et al. the inventors have developed an industrially applicable process for preparing poly(lactide-co-glycolide) copolymer particles with a certain lactide:glycolide ratio. During their studies it has been found that the known processes from Kongsombut et al. and Mishima et al. could not be simply scaled up for the PLGA polymers used either due to far too low yields (see working example 3b). It was not to be foreseen from these authors that a process for preparing PLGA particles with an average particle size from 50-800 nm and with a content of polymerized glycolide units of 20 to 45% by weight of the copolymer and a molecular weight $M_w$ of 1.000-25.000 could be developed with yield high enough to satisfy industrial economic needs.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

FIGURES

FIG. 1

Figure 2:
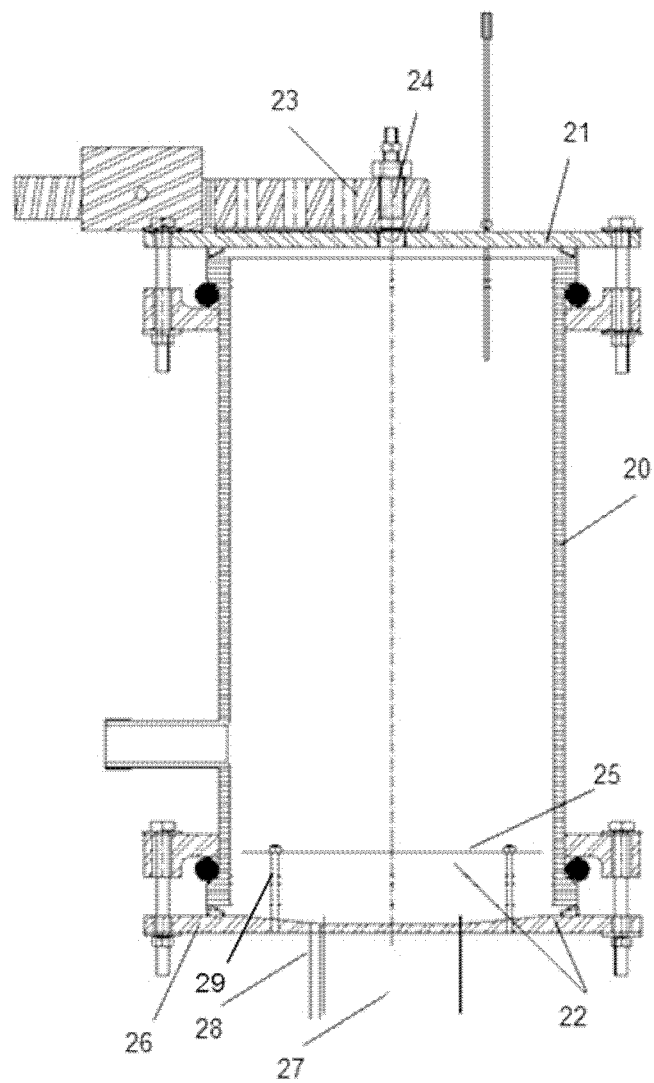
FIG. 2 is a schematic drawing of the second reactor.

Schematic map for an inventive process and equipment
1=Gas cylinder with carbon dioxide
2=Cooling unit (heat exchanger with cryostate)
3=Pump for carbon dioxide (membrane pump)
4=Container with ethanol
5=Pump for ethanol (HPLC pump)
6=T-mixer for mixing carbon dioxide and ethanol
7=Filter/mixing unit
8=Heat exchanger
9=Pressure control valve (PCV)
10=Pressure regulation unit
11=First reactor
12=Standpipe
13=Heated capillary nozzle (Inlet)
14=Second reactor
15=Outlet for carbon dioxide/ethanol aerosol
16=Outlet for ethanolic PLGA-particle suspension 17=Stirring equipment
FIG. 2
Schematic drawing of the second reactor (14)
20=Wall of the second reactor (14)
21=Upper plate
22=Bottom plate (with upper sheet (25) and lower sheet (26)=double sheeted bottom plate)
23=Heater
24=Drill for the spray nozzle
25=Upper sheet of the bottom plate
26=Lower sheet of the bottom plate
27=Outlet for the gas flow
28=Outlet for the liquid flow (particle dispersion)
29=Distance element (distance holder)

DETAILED DESCRIPTION OF THE INVENTION

The invention is concerned with a batch process or a semi-continuous or a continuous process for preparing poly (lactide-co-glycolide) copolymer nanoparticles comprising the steps:
  a) transfer of ethanol and a poly(lactide-co-glycolide) copolymer with a content of polymerized monomer units of 55-80 mol % lactide and 20 to 45 mol % of glycolide and a molecular weight $M_w$ of 1.000-25.000 into a first reactor with a stirring equipment,
  b) feeding carbon dioxide into the first reactor so that carbon dioxide is from 65 to 85% by weight and the ethanol is 15 to 35% by weight whereby carbon dioxide and ethanol add up to 100%,
  c) mixing the poly(lactide-co-glycolide) copolymer, the ethanol and the carbon dioxide by stirring and adjusting or maintaining the mixture in the first reactor to a temperature of at least 31 and up to 70° C. and a pressure of at least 7.38 and up to 50 MPa, where carbon dioxide enters the supercritical stage with ethanol as a co-solvent,
  d) stirring the mixture from step c) for 1 to 5 hours, whereby at least a part of the poly(glycolide-co-lactide) copolymer becomes dissolved in the mixture of carbon dioxide and ethanol,
  e) transfer of the mixture from step d) into a second reactor under rapid reduction of the pressure and expansion with phase separation into carbon dioxide gas and ethanol aerosol and an ethanolic suspension containing poly(glycolide-co-lactide) copolymer particles
  f) removal of the carbon dioxide gas and the ethanol aerosol from the second reactor
  g) obtaining the poly(glycolide-co-lactide) copolymer particles with an average particle size in the range of 50-800 nm in the form of an ethanolic suspension or in dry form from the second reactor.

The poly(lactide-co-glycolide) copolymer (PLGA) particles obtained from the process as disclosed may show an average particle size from 50 to 800, 100 to 500, 200 to 400 nm. The average particle size of the PLGA particles may preferably be determined by dynamic light scattering (DLS).

The yield of PLGA particles that may be obtained in step g) may be at least 4, at least 5, at least 6, at least 8, at least 10, at least 20, at least 30, at least 35, at least 50% by weight relative to the applied amount of poly(lactide-co-glycolide) copolymer in step a). The yield of PLGA particles may be in the range from 4 to 50, 6 to 99, 8 to 95, 10 to 80, 20 to 70, 20 to 60, 25 to 50, 30 to 48% by weight relative to the applied amount of poly(lactide-co-glycolide) copolymer in step a).

A semi-continuous process shall mean that the process may be performed by stepwise or continuously adding or feeding carbon dioxide and ethanol to the stock of the poly(lactide-co-glycolide) copolymer in the first reactor where at least one component, e.g. carbon dioxide, of the solvent mixture is near critical or supercritical, and at least partially transferring the solvent mixture with the dissolved or dispersed poly(lactide-co-glycolide) copolymer from the first reactor to the second reactor (stepwise or continuously), where the mixture is expanded.

A continuous process shall mean that the process may be run by stepwise or (semi-)continuously adding or feeding the poly(lactide-co-glycolide) copolymer, the carbon dioxide and the ethanol into the first reactor, where at least one component (e.g. carbon dioxide) of the solvent mixture is near- or supercritical, and at least partially transferring the solvent mixture with the dissolved or dispersed poly(lactide-co-glycolide) copolymer from the first reactor to the second reactor (stepwise or continuously), where the mixture is expanded.

A poly(lactide-co-glycolide) copolymer (PLGA) is a copolymer that may be polymerized from glycolide and lactide by ring opening polymerization in the presence of a catalyst, such as stannous octanoate. A suitable poly(lactide-co-glycolide) copolymer may have a content of polymerized monomer units of 55 to 80, 70 to 80 mol % of lactide and 20 to 45, 20 to 30 mol % of glycolide.

The molecular weight $M_w$ of the PLGA may be in the range of 1.000-50.000, 1.000 to 30.000, 1.000 to 25.000, 2.000 to 25.000, 1000 to less than 30.000, less than 30.000, 2.000 to 29.000, 5.000 to 28.000, 3.000-20.000, 4.000 to 15.000, 8.000 to 12.000. The molecular weight $M_w$ of the PLGA may be determined by chromatography in tetrahydrofuran (THF) for instance relative to polystyrene standards or poly(lactic acid)-standards.

For the process as disclosed a very suitable commercially available PLGA polymer is for instance RESOMER® RG 752H which is a poly(D,L-lactide-co-glycolide) 75:25 (mol ratio) copolymer with a molecular weight Mw in the range of 4.000-15.000, 8.000-12.000.

PLGA Particles Obtained from the Inventive Process

The poly(lactide-co-glycolide) copolymer particles obtained from the process as disclosed show a storage stability in ethanolic suspension of at least two months in respect to constant particle size and absence of aggregation.

The average particle size of the PLGA particles may be in the range of 50-800, 100-600, 200-500 nm. The average particle size and the polydispersity index (PI) may be determined by dynamic light scattering (DLS) preferably using a Malvern Nanosizer and according to ISO standards document 13321:1996 E and ISO 22412:2008.

The polydispersity-index (PI) of the PLGA particles may be 0.5 or less, 0.2 or less, 0.1 or less, 0.01 to 0.2, 0.02 to 0.1, 0.03 to 0.08 when the PI is determined by dynamic light scattering (DLS) according to ISO 13321.

Process Steps

The description of the process steps a) to g) shall be understood in that they may be performed one after another as a batch process or in the case of a semi-continuous process or a continuous process at least partially simultaneous or simultaneously.

Step a):
In step a) ethanol and a poly(lactide-co-glycolide) copolymer with a content of polymerized monomer units of 55-80 mol % lactide and 20 to 45 mol % of glycolide and a molecular weight $M_w$ of 1.000-25.000 are transferred or put into a first reactor with a stirring equipment.

The relation of ethanol and a poly(lactide-co-glycolide) copolymer may be 90 to 99.9, 95 to 99.9, 98 to 99.9, 99 to 99.2% by weight ethanol and 0.1 to 10, 0.1 to 5, 0.1 to 2, 0.2 to 1% by weight poly(lactide-co-glycolide) copolymer wherein ethanol and a poly(lactide-co-glycolide) copolymer add up to 100%.

At this stage the PLGA copolymer may be usually in the form of a nugget, a lump or a granulate.

The first reactor (11) may also be designated as the extraction reactor.

The first reactor (11) is a reactor that is preferably capable to safely withstand high pressure of at least 20 MPa or more, 20 to 100 MPa, or at least 100 MPa or even more, e.g. a high-pressure reactor or extractor. For example autoclave equipment may be used as the first reactor (11). The first reactor (11) may be preferably double-walled and able to be tempered and pressured.

The stirring equipment (17) may be a stirrer with a motor, which is usually positioned on the top of the first reactor (11) and reaches from there into the reactor into solvent/polymer mixture. The typical stirrer may be equipped at its end with stirrer blades, propellers or an anchor and may be rotated with a rotational speed in the range of 20 to 100, 50 to 250, 100 to 1000, 300-700 rpm. 500 rpm (rounds per minute) may be very suitable for a first reactor with a volume of for instance about 0.1 to 10, 10 to 100, 100 to 300, 150 to 1000 liter.

Optionally an active pharmaceutical ingredient may be added in step a).

Step b):

In step b) carbon dioxide is fed into the first reactor (11) so that carbon dioxide is from 65 to 85, 70-75% by weight and the ethanol is 15 to 35, 25 to 30% by weight wherein carbon dioxide and ethanol add up to 100%.

When the process is started the mixture of carbon dioxide and ethanol may be adjusted by heating and pressuring in the first reactor (11) to a temperature of at least 31 and up to 70° C., 31 and up to 50° C. and a pressure of at least 7.38 and up to 50 MPa, preferably to about 35 to 45, 38 to 43° C. and a pressure of about 10 to 30, 15 to 25, 18 to 22 MPa, where carbon dioxide is in the supercritical stage with ethanol as co-solvent (ethanol functions as a co-solvent).

When the process is run semi-continuously or continuously the mixture of carbon dioxide and ethanol is fed into the first reactor (11) whereby carbon dioxide is near to the supercritical stage or already in the supercritical stage to substitute solvent mixture (including the PLGA polymer dissolved or dispersed therein) that is transferred from the first reactor (11) to the second reactor (14).

Thus when the process is run semi-continuously or continuously the mixture of carbon dioxide and ethanol is fed into the first reactor (11) and maintained there at a temperature of at least 31 and up to 50° C. and a pressure of at least 7.38 and up to 50 MPa, preferably to about 35 to 45, 38 to 43° C. and a pressure of about 10 to 30, 15 to 25, 18 to 22 MPa, where carbon dioxide is supercritical and ethanol is the co-solvent (ethanol functions as a co-solvent).

Step c):

In step c) the poly(lactide-co-glycolide) copolymer, the ethanol and the carbon dioxide in the first reactor (11) are mixed by stirring and the mixture is adjusted or maintained to a temperature of at least 31 and up to 50° C. and a pressure of at least 7.38 and up to 50 MPa, preferably at about 35 to 45, 38 to 43° C. and a pressure of about 10 to 30, 15 to 25, 18 to 22 MPa, where carbon dioxide is supercritical and ethanol is the co-solvent (ethanol functions as a co-solvent). A very suitable temperature/pressure combination may be 41° C. and 20 MPa. The mixture of supercritical carbon dioxide and ethanol (in the following we denote such mixture with at least one supercritical component as supercritical solvent mixture) is capable to function as a solvent for the poly(lactide-co-glycolide) copolymer. The poly(lactide-co-glycolide) copolymer would be not soluble or only poorly soluble in supercritical carbon dioxide alone or in ethanol alone.

To provide $CO_2$ in its supercritical state its critical temperature of 31.0° C. and critical pressure of 7.38 MPa must be reached or exceeded. Before pressurizing the $CO_2$ from about 6 MPa in a gas cylinder ((1), stock bottle) up to for instance 20 MPa in the first reactor, the carbon dioxide may be cooled in a cooling unit (2), preferably down to minus 5 to minus 15° C., preferably to about minus 10° C. (−10° C.), because it heats up during the compression with the membrane pump. After removal from the gas cylinder with carbon dioxide (1), the gas may be cooled down using a heat exchanger which is tempered by a cryostat (2). A pressure regulation unit (10) may be installed to ensure a constant pressure in the first reactor (11). The pressure regulation unit (10) may have a bypass between the suction side and the pressure side of a pump for carbon dioxide (3) and may be equipped with a pressure control valve (PCV) (9). The desired pressure of the supercritical fluid may be then set at the PCV (9).

A continuous feed of the co-solvent ethanol may be provided by a HPLC pump (5). The pressurized $CO_2$ and ethanol as co-solvent flows may be merged within a T-mixer (6) and the mixed solvents are heated with a heat exchanger (8) before entering the first reactor (11). Within the first reactor (11) the supercritical solvent mixture is stirred and gets saturated with the polymer.

Step d):

In step d) the mixture from step c) may be stirred for 1 to 5, 2 to 4 hours, whereby at least a part of the poly(lactide-co-glycolide) copolymer becomes dissolved in the supercritical solvent.

The pressure in the first reactor (11) may be 10 to 30, 15 to 25, 18 to 22 MPa. The temperature may be 35 to 45, 38 to 43° C. A very suitable temperature/pressure combination may be 41° C. and 20 MPa.

The stirring speed may be 10-1000, 20-800, 300-700 rpm (rounds per minute). 50 rpm may be very suitable for a first reactor with a volume of about 100 liter.

The process may be run in a way that only a part of the poly(lactide-co-glycolide) copolymer becomes dissolved in step d) and simultaneous to the transfer of the mixture from the first reactor (11) into the second reactor (14) in step e) a mixture of ethanol and carbon dioxide is added to the first reactor (11), so that a part or all of the previously undissolved poly(lactide-co-glycolide) copolymer becomes dissolved.

Step e):

In step e) the mixture from step d) is transferred respectively sprayed into a second reactor (14) under rapid reduction of the pressure and expansion with phase separation into a gas phase (mainly carbon dioxide) and an aerosol (mainly ethanol) and an ethanolic suspension (solid phase) containing poly(lactide-co-glycolide) copolymer particles. Through the rapid expansion of the supercritical solvent mixture and loss of the supercritical stage the previously dissolved poly(lactide-co-glycolide) copolymer separates and disperses into particles of distinct average particle size and size distribution in the ethanolic phase. Rapid reduction of the pressure shall mean that the pressure of the mixture is reduced to atmospheric pressure rapidly, preferably within less than sixty seconds, less than ten seconds or less than one second. Due to rapid reduction of the pressure a phase separation of the mixture into a gas phase and an aerosol and an ethanolic suspension containing poly(lactide-co-glycolide) copolymer particles takes place.

The mixture from step d), which we denote in the following as a supercritical solution of the polymer, may leave the first reactor through a standpipe and may be expanded through a heated capillary nozzle to atmospheric pressure. The resulting aerosol may be then collected in the second reactor, which may be a vented glass cylinder. The second reactor may be provided with a suction pump to generate atmospheric pressure or a pressure below atmospheric pressure. The remaining ethanolic poly(lactide-co-glycolide) copolymer particle suspension may be removed from the second reactor through a drain hose and may be collected in a container.

The second reactor (14) may be also designated as the spraying chamber.

The second reactor (14) may be made of a cylinder (glass or plastic) with both ends closed by plates (21, 22), preferably metal plates. The upper plate (21) may carry a heater (23) with a drill for the spray nozzle (24) which is connected to the second vessel (14). The heater (23) is controlled via the process control system (PCS). In order to take samples of the sprayed product a fitting may be included. The bottom plate (22) may be single sheeted or preferably comprise two sheets (25, 26) where the usually horizontally mounted upper sheet (25) is not in contact with the (vertical) wall (20) of the second reactor (14) and the bottom sheet (26) has two outlets (27, 28) one for the gas flow (27) and the second one for liquid particle dispersion (28). Because of the double sheeted bottom plate (22) the ethanolic aerosol stays longer in the cylinder and there is enough time for the PLGA particles to move from the aerosol phase to the liquid ethanol phase and to be collected through the outlet (28), whereas the $CO_2$ gas is pumped out of cylinder through the gas outlet (27).

The pressure and the temperature of supercritical solution of the polymer drop rapidly, preferably within less than 1 second, below the critical values 7.38 MPa and 31° C. in the second reactor. Pressure and temperature of the second reactor then may be at ambient conditions or slightly under ambient pressure (about 100-1013 mbar) and at room temperature or slightly below room temperature because of the expansion process (may be in the range of 5-25° C.). The advantages of a slight underpressure is that the case of an inclusion of an active ingredient in the process the distribution of this active ingredient outside of the second reactor is prevented for health reasons of operators.

Step f):

In step f) carbon dioxide gas (gas phase with mainly carbon dioxide) and ethanolic aerosol are removed from the second reactor. An ethanolic suspension containing the poly(lactide-co-glycolide) copolymer in the form of particles remains in the second reactor.

Step q):

In step g) the PLGA particles with an average particle size in the range of 50-800 nm preferably in the form of an ethanolic suspension are obtained from the second reactor. When the second reactor is an aerocyclone the PLGA particles with an average particle size in the range of 50-800 nm may be obtained in the form of an ethanolic suspension or preferably directly in dry form (e.g. powder).

Process step g) may be followed by another process step wherein the poly(lactide-co-glycolide) copolymer particles are obtained from the ethanolic suspension from step g) in dry form by evaporation of the ethanol, preferably by spray drying.

The particle suspension in ethanol may be mixed with an aqueous solution of about 0.1 to 2 wt. % preferably 1 wt. % PVA in the ratio of 1:4 to 4:1, preferably 1:1. Before running the spray drying process, 0.5 to 5 wt-%, preferably 2 wt-% of D-Mannit may be added to the mixture. The inlet air temperature may be set to 40 to 70, preferably 60° C. and the air flow may be 50 to 200, preferably 130 L/min. The dried particles that may be obtained are fully redispersible in water at room temperature without visible agglomeration.

Poly(Lactide-Co-Glycolide) Copolymer Particles Comprised in the Gas Phase and/or the Ethanolic Aerosol It has been found that although the yields of the poly (lactide-co-glycolide) copolymer particles obtained in the second reactor in the form of an ethanolic suspension in step g) are quite satisfactory they are usually far below 100%. After investigation almost no remaining poly(lactide-co-glycolide) copolymer could be found in the first reactor. This leads to the conclusion that the gas phase and/or the ethanolic aerosol may still comprise certain or even considerable amounts of poly(lactide-co-glycolide) copolymer particles. This leaves room for further improvement. In a preferred embodiment of the invention these particles may be obtained additionally from the gas phase and/or the ethanolic aerosol by suitable separation techniques such as the use of an aero-cyclone. Thus poly(lactide-co-glycolide) copolymer particles comprised in the gas phase and/or the ethanolic aerosol which is removed from the second reactor in step f) may be obtained from the gas phase and/or the ethanolic aerosol by suitable separation techniques such as the use of an aero cyclone, preferred an aero-cyclone with electrostatical recirculation system. By such an additional treatment the overall yield of poly(lactide-co-glycolide) copolymer particles may be improved considerably and may be in the range of 6 to 100, 30 to 100, 8 to 80, 10 to 50, 15 to 50, 20 to 50% or may become even up to 100% (% by weight relative to the amount of poly(lactide-co-glycolide) copolymer applied in step a)

Batch, Semi-Continuous or Continuous Process

The process may be run as a batch process without further addition or substitution of the removed mixture of carbon dioxide and ethanol or poly(lactide-co-glycolide) copolymer.

The process as disclosed may be preferably preformed in a semi-continuous manner wherein a part of the poly(lactide-co-glycolide) copolymer becomes dissolved in step d) and simultaneous to the transfer of the mixture from step d) into the second reactor (14) in step e) a mixture of ethanol and carbon dioxide in supercritical stage is added to the first reactor (11), so that a part or all of the undissolved poly (lactide-co-glycolide) copolymer becomes dissolved.

Preferably the addition of the mixture of ethanol and supercritical carbon dioxide into the first reactor (11) and the simultaneous transfer of the mixture from step d) into the second reactor (14) in step e) may be continued until the poly(lactide-co-glycolide) copolymer was dissolved to an amount of at least 98, 99 or 100% and discharged to the second reactor in step e) followed by steps f) and g).

The process as disclosed may preferably be performed in a continuous manner by continuously adding the poly(lactide-co-glycolide) copolymer, the carbon dioxide in supercritical stage and the ethanol into the first reactor (11), transferring the mixture into the second reactor (14) and separating the gas phase and the poly(lactide-co-glycolide) copolymer particles in ethanolic suspension.

In the processes disclosed the poly(lactide-co-glycolide) copolymer particles may be obtained in the form of an ethanolic suspension or in dry form (e.g. powder).

Device

The invention further discloses a device for carrying out a process as disclosed.

The device for carrying out a process as disclosed comprises or essentially comprises a first reactor (11) and a second reactor (14), means for mixing, cooling, heating and pressurizing carbon dioxide and ethanol and feeding the same into the first reactor and means for the transfer of the mixture of carbon dioxide, ethanol and poly(lactide-co-glycolide) copolymer particles into the second reactor, wherein the second reactor is equipped with outlets for the gas flow (carbon dioxide gas and ethanol aerosol) and for the liquid flow (particle dispersion=ethanolic particle dispersion or suspension) and a bottom plate (22), preferably with a double-sheeted bottom plate (22), with an upper sheet (25) and a lower sheet (26), where the edges of the upper sheet (25) are preferably not in contact with the vertical wall of the second reactor (14, 20).

Between the upper sheet (25) and the lower sheet (26) of the bottom plate (22) there may be a distance of for instance 1 to 20, 2 to 15, 3 to 10 cm. The upper sheet (25) is preferably not in contact with the (vertical) wall (20) of the second reactor (14). The distance may be realized by use of distance elements or distance holders like screws or bolts or the like.

Less preferred but also possible the upper sheet (25) may be fastened in its position by holders located on the vertical wall of the reactor as long as sufficient room between edges of the upper sheet (25) and the reactor wall (20) remains so that aerosol may pass finally to the bottom of the second reactor (14).

Figure 1:
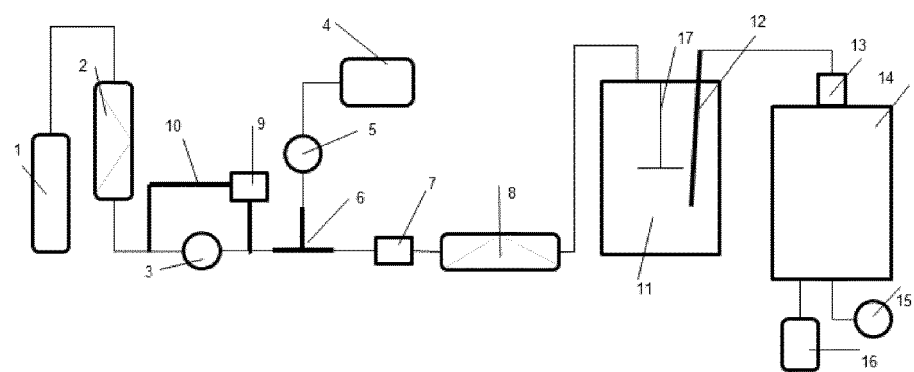
FIG. 1 is a schematic map for an inventive process and equipment.

The means for mixing, cooling, heating and pressuring carbon dioxide and ethanol and feeding the same into the first reactor (11) and means for the transfer of the mixture of carbon dioxide, ethanol and poly(lactide-co-glycolide) copolymer particles into the second reactor (14) preferably comprise the elements as shown in FIG. 1:

1=Gas cylinder with carbon dioxide
2=Cooling unit (heat exchanger with cryostate)
3=Pump for carbon dioxide (membrane pump)
4=Container with ethanol
5=Pump for ethanol (HPLC pump)
6=T-mixer for mixing carbon dioxide and ethanol
7=Filter/mixing unit
8=Heat exchanger
9=Pressure control valve (PCV)
10=Pressure regulation unit
12=Standpipe
13=Heated capillary nozzle (Inlet)
15=Outlet for carbon dioxide/ethanol aerosol
16=Outlet for ethanolic PLGA-particle suspension
17=Stirring equipment When the second reactor (14), is not an aero cyclone it may be described as follows: The second reactor (14) may be preferably made of a cylinder (glass or plastic) with both ends closed by plates (21, 22) preferably metal plates. The upper plate (21) may carry a heater (23) with a drill for the spray nozzle (24) which is connected to the second vessel (14). The heater (23) is controlled via the PCS system. In order to take samples of the sprayed product a fitting may be included. The bottom plate (22) may be single sheeted and consist of only one (lower) sheet (26). Preferably the bottom plate is a double sheeted bottom plate (22) comprising two sheets, an upper sheet (25) and a lower sheet (26) where the upper sheet (25) is preferably not in contact with the (vertical) wall (20) of the second reactor (14) and the lower sheet (26) has two outlets (27, 28) one for the gas flow (27) and the second one for liquid particle dispersion (28).

The upper sheet (25) has preferably a circular geometry and is placed in the middle to fit to the cylindrical geometry of the reactor. The upper sheet is usually mounted horizontally preferably by distance holders (29) in parallel onto the lower sheet (26). The distance of the edges of the upper sheet (25) to the (vertical) reactor wall (20) may be in the range of 0.25 to 10, 0.5 to 2, 0.7 to 1.5 cm. Between the upper sheet (25) and the lower sheet (26) of the bottom plate (22) there may be a distance of for instance 1 to 20, 2 to 15, 3 to 10 cm.

Because the upper sheet (25) is not in contact with the wall (20) the liquid may flow down between upper sheet (25) and the wall (20) and thus assemble in the room between the upper (25) and the lower sheet (26) which supports an effective separation of the liquid phase (ethanolic suspension) from the gas phase (comprising mainly carbon dioxide and/or in the ethanolic aerosol).

With an upper sheet (25) installed in the second reactor (14) the yield of particles may be improved to about 5 to 15 or 10 to 25% in comparison to a second reactor with a bottom plate consisting of a lower plate (26) only but without an upper sheet (25). This is shown in examples 1a,b in comparison to example 1c.

Because of the double sheeted bottom plate (22) the ethanolic aerosol stays longer in the cylinder and there is enough time for the PLGA particles to move from the aerosol phase to the liquid ethanolic phase and to be collected through the outlet (28), whereas the $CO_2$ gas is pumped out of cylinder through the gas outlet (27).

An aero cyclone may be placed down-stream behind the second reactor, which is not an aero cyclone, so that the gas flow from the second reactor may be fed into the aero cyclone. The gas flow may comprise the gas phase comprising mainly carbon dioxide and/or ethanolic aerosol. The gas flow may further comprise poly(lactide-co-glycolide) copolymer respectively poly(lactide-co-glycolide) copolymer particles.

Poly(lactide-co-glycolide) copolymer particles which are not comprised in the ethanolic suspension but still comprised in the gas phase and/or in the ethanolic aerosol which is removed from the second reactor in step f) may be obtained by suitable separation techniques such as the use of an aero cyclone, preferably by the use of an aero cyclone with electrostatical recirculation system. The aero cyclone, preferably an aero cyclone with electrostatical recirculation system may be used in addition to the second reactor. In this case the stream comprising the gas phase and/or the ethanolic aerosol is lead from the second reactor into the aero cyclone.

Usually the second reactor (14) is not an aero cyclone. However alternatively the second reactor may be substituted by an aero cyclone, preferably by an aero cyclone with electrostatical recirculation system. In this case the expanded supercritical mixture from the first reactor in step d) is in step f) directly sprayed into the second reactor which is an aero cyclone. Thus, the aero cyclone becomes the second reactor. A high yield of poly(lactide-co-glycolide) copolymer particles may be obtained from the aero cyclone.

Aero Cyclone

In the process as disclosed, poly(lactide-co-glycolide) copolymer particles which are still comprised in the gas phase and/or the ethanolic aerosol which is removed from the second reactor in step f) may be are obtained by suitable separation techniques such as the use of an aero cyclone (aero cyclone equipment/cyclonic separation), preferably by the use of an aero cyclone with electrostatical recirculation system.

Cyclonic separation is a method of removing particles from an air, gas or liquid stream, preferably without the use of filters, through vortex separation. Cyclonic separation techniques and equipment are well known to person skilled in the art.

The device for carrying out the process as disclosed may comprise a first reactor and a second reactor, means for mixing, cooling, heating and pressuring carbon dioxide and ethanol and feeding the same into the first reactor and means for the transfer of the mixture of carbon dioxide, ethanol and poly(lactide-co-glycolide) copolymer particles into the second reactor, wherein the second reactor is an aero cyclone.

EXAMPLES

Polymers Used in the Examples

RESOMER® RG503H is a poly(D,L-lactide-co-glycolide) 50:50 (mol ratio) with a molecular weight Mw of about 27.400 kDa (measured by gel chromatograpy in tetrahydrofuran (THF) relative to polystyrene standards).

RESOMER® RG 752H is a poly(D,L-lactide-co-glycolide) 75:25 (mol ratio) copolymer with a molecular weight Mw of about 11.200 kDa (measured by gel chromatography in tetrahydrofuran (THF) relative to polystyrene standards).

RESOMER® RG 753H is a poly(D,L-lactide-co-glycolide) 75:25 (mol ratio) copolymer with a molecular weight Mw of about 32.800 kDa (measured by gel chromatography in tetrahydrofuran (THF) relative to polystyrene standards).

RESOMER® RG858S is a poly(D,L-lactide-co-glycolide) 85:15 (mol ratio) copolymer with a molecular weight Mw of about 154.000 kDa (measured by gel chromatography in tetrahydrofuran (THF) relative to polystyrene standards).

RESOMER® Select 8515 DLG 5A is a poly(D,L-lactide-co-glycolide) 85:15 (mol ratio) copolymer with a molecular weight Mw of about 62 kDa (measured by gel chromatography in tetrahydrofuran (THF) relative to polystyrene standards).

The RESOMER® type RESOMER® RG858S carries an ester end group, while the RESOMER® types RESOMER® RG503H, RESOMER® RG 752H and RESOMER® RG 753H and RESOMER® Select 8515 DLG 5A carry an acid end group.

Description of the RESS Device and the Process

For the semi-continuous RESS-process (Rapid Expansion of Supercritical Solution) the following equipment was used: MidiClave type 3/500 ml double-walled high pressure reactor (Büchi Glas Uster AG, Uster, Switzerland) including a magnetic stirrer, a $CO_2$ pump (LDB 1, LEWA GmbH, Leonberg, Germany), an orifice nozzle with a diameter of 0.1 mm as well as a HPLC pump 64 (Knauer GmbH, Berlin, Germany). The materials used were liquefied carbon dioxide (Biogon® C E290, Linde AG, Germany), Ethanol absolute (Merck KGaA, Germany), poly-(lactic-co-glycolic acid) Resomer® RG 503 H, Resomer® RG 752 H, Resomer® RG 858 S, Resomer® Select 8515 DLG 5A and Resomer® RG 753 H (Nutrition & Care GmbH, Germany), D-Mannit (Carl Roth GmbH & Co. KG, Germany) and Mowiol 4-88 (polyvinyl alcohol Carl Roth GmbH & Co. KG). For the drying of the produced particles a Nano B-90 spray dryer (Büchi AG, Switzerland) was used.

To provide $CO_2$ in its supercritical state its critical temperature of 31.0° C. and its critical pressure of 7.38 MPa must be exceeded. Before pressurizing the $CO_2$ from 6 MPa in the stock bottle up to 20 MPa in the reactor, the gas is cooled down to −10° C., because it heats up during the compression with the membrane pump. Directly after removal from the stock bottle the gas is cooled down using a heat exchanger which is tempered by a cryostat. To ensure a constant pressure in the reactor a pressure regulation unit was installed. This unit consists of a bypass between the suction side and the pressure side of the pump, which is equipped with a pressure control valve (PCV). The desired pressure of the supercritical fluid is set at the PCV. The continuous feed of the co-solvent is provided by a HPLC pump. The pressurized $CO_2$ and co-solvent flows are merged within a T-mixer and the mixed solvents are heated with a heat exchanger before entering the double-walled and tempered extraction reactor. Within the high pressure reactor the supercritical mixture is stirred and gets saturated with the polymer. The supercritical solution of the polymer leaves the extractor through a standpipe and is expanded through a heated capillary nozzle to atmospheric pressure. The aerosol is collected within a vented glass cylinder, which is provided with a suction pump to generate a low atmospheric pressure. The product suspension is removed from the spraying chamber through a drain hose and is collected in a container.

Design of the Second Reactor

The second reactor (14) or second vessel may be made of a cylinder (glass or plastic) with both ends closed by plates (metals). On the upper plate (21) a heater with a drill for the spray nozzle (24) is connected to the second reactor (14). A heater (23) is controlled via the PCS system. In order to take samples of the sprayed product a fitting. The bottom plate (22) comprises two sheets whereas the upper sheet (25) is preferably not connected to the vertical wall (20) of the second reactor. The lower sheet (26) of the bottom plate (22) has two outlets (27, 28) one for the gas flow (27) and the second one (28) for liquid particle dispersion. Because of the bottom plate (22) which comprises the two sheets (25, 26) the sprayed aerosol stays longer in the cylinder and the particles have enough time to assemble in the liquid ethanol phase whereas the $CO_2$ gas is pumped out of cylinder through the gas outlet (27). Between the upper sheet (25) and the lower sheet (26) there may be a distance of for instance 1 to 20, 2 to 15 cm. The distance may be realized by use of distance elements (29) or distance holders like screws or bolts or the like.

Example 1a (Inventive)

The RESS-device as described above was used to process Resomer® RG 752 H ($M_w$ 11.2 kDa, measured in THF relative to polystyrene standards; 25 mol % glycolide) according to the procedure shown in FIG. 1. 0.7 g of PLGA and 130.0 g of ethanol (co-solvent) were filled into the reactor. After sealing the reactor, it was pressurized with 434.5 g of $CO_2$. The temperature of the mixture was set to 40° C. and the pressure was 20 MPa. Whilst maintaining these conditions, the supercritical solvent mixture was stirred for 3 hours with a rotational speed of 500 rpm. After that period the supercritical solution was expanded through the orifice as the pressure in the reactor and the ratio of solvent to co-solvent remained constant over the spraying time. The orifice was heated to 240° C. and the spraying time was 1 hour. A dynamic light scattering (DLS) method was used to measure the size distribution and the mean diameter of the produced particles. The particle mean diameter was 320 nm and the polydispersity index (PI) was 0.048. The suspension of the particles in ethanol was stable for a period of at least 2 months without any change in size or morphology. For SEM (scanning electron microscope) analysis the suspension was diluted 1:5 with ethanol absolute and one droplet was dried directly on a sample carrier. After sputtering with gold, the sample was analyzed by SEM analysis. The yield of particles that were obtained by the process and collected in the container was 40 wt. % relative to the applied amount of polymer.

Example 1b (Inventive (Repetition of Example 1a))

The RESS-device as described above was used to process Resomer® RG 752 H (Mw 11.2 kDa, measured in THF relative to polystyrene standards; 25 mol % glycolide) according to the procedure shown in FIG. 1. 0.7 g of PLGA and 130.0 g of ethanol (co-solvent) were filled into the reactor. After sealing the reactor, the reactor was pressurized with 430 g of $CO_2$. The temperature of the mixture was set to 40° C. and the pressure was 18.7+/−0.1 MPa during manufacturing. Whilst maintaining these conditions, the supercritical solvent mixture was stirred for 3 hours with a rotational speed of 500+/−20 rpm. After that period the supercritical solution was expanded through the orifice as the pressure in the reactor and the ratio of solvent $CO_2$ (77+/−0.9%) to co-solvent ethanol (23+/−0.9%) remained constant over the spraying time. The orifice was heated to 240+/−2° C. and the spraying time was 1 hour 1 min. A dynamic light scattering (DLS) method was used to measure the size distribution and the mean diameter of the produced particles. The particle mean diameter was 219 nm and the polydispersity index (PI) was 0.18. The yield of particles that were obtained by the process and collected in the container was 46 wt. % relative to the applied amount of polymer.

Example 1c—(Inventive (Reactor 2 without the Upper Sheet of the Bottom Plate))

The same RESS-device as described above was used but without the upper sheet (25) of the bottom plate (22). The RESS device was used to process Resomer® RG 752 H (Mw 11.2 kDa, measured in THF relative to polystyrene standards; 25 mol % glycolide) according to the procedure shown in FIG. 1. 0.7 g of PLGA and 130.0 g of ethanol (co-solvent) were filled into the reactor. After sealing the reactor, the reactor was pressurized with 437 g of $CO_2$. The temperature of the mixture was set to 40° C. and the pressure was 18.6+/−0.1 MPa. Whilst maintaining these conditions, the supercritical solvent mixture was stirred for 3 hours with a rotational speed of 500+/−20 rpm. After that period the supercritical solution was expanded through the orifice as the pressure in the reactor and the ratio of solvent $CO_2$ (77+/−0.9%) to co-solvent ethanol (23+/−0.9%) remained constant over the spraying time. The orifice was heated to 240+/−0.6° C. and the spraying time was 1 hour 2 min. A dynamic light scattering (DLS) method was used to measure the size distribution and the mean diameter of the produced particles. The particle mean diameter was 192 nm and the polydispersity index (PI) was 0.17. The yield of particles that were obtained by the process and collected in the container was 37 wt. % relative to the applied amount of polymer.

Example 2 (Comparative)

Particles were produced as described in example 1a, but with the use of Resomer® RG 753 H ($M_w$ 32.8 kDa, measured in THF relative to polystyrol standards; 25% glycolide) instead of RG 752 H. The particle mean diameter was 393 nm and the polydispersity index (PI) was 0.015. The yield of particles that were obtained by the process and collected in the container was 5 wt.-% relative to the applied amount of polymer.

Example 3a (Comparative)

Particles were produced as described in example 1a, but with the use of Resomer® RG 858 S ($M_w$ 154 kDa, measured in THF relative to polystyrene standards; 15% glycolide) instead of RG 752 H. The particle mean diameter was estimated using image analysis software, which were taken with a scanning electron microscope (SEM). The mean diameter of 100 counted particles was 250 nm and the particle size distribution ranged between 200 nm and 300 nm. Overall the particles looked uniformly in size and had a spherical shape. The yield of particles that were obtained by the process and collected in the container was 2 wt.-% relative to the applied amount of polymer.

Example 3b (Comparative (Lower Molecular Weight than in Example 3a))

Particles were produced as described in example 1b (repetition), but Resomer® Select 8515 5A (Mw 62 kDa, measured in THF relative to polystyrene standards) has been used instead of RG 752 H. The orifice was heated to 240+/−0.2° C. The pressure in reactor 1 was set to 18.5+/−0.2 MPa. The ratio of solvent $CO_2$ (78+/−1.8%) to co-solvent ethanol (22+/−1.8%) remained constant over the spraying time. A dynamic light scattering (DLS) method was used to measure the size distribution and the mean diameter of the produced particles. The particle mean diameter was 169 nm and the polydispersity index (PI) was 0.048. The yield of particles obtained by the process and collected in the container was 5.9 wt.-% relative to the applied amount of polymer.

Example 4 (Inventive)

Particles were produced as described in example 1a using Resomer® RG 752 H (Mw 11.2 kDa, measured in THF relative to polystyrene standards; 25 mol % glycolide), but the amount of polymer used was 1.4 g instead of 0.7 g. The DLS particle mean diameter was 366 nm and the PI was 0.036. The yield of particles that were obtained by the process and collected in the container was 37 wt.-% relative to the applied amount of polymer. In order to receive a dry powder with a high stock stability, the particle suspension was dried by spray drying as described in the following. The particle suspension in ethanol was mixed with an aqueous solution of 1 wt. % PVA in the ratio of 1:1. Before running the spray drying process, 2 wt.-% of D-Mannit were added to the mixture. The inlet air temperature was set to 60° C. and the air flow was 130 L/min. The dried particles were fully redispersible in water without visible agglomeration.

Example 5 (Comparative)

The process was run according to the procedure of example 1 a, but with the use of Resomer® RG 503 H ($M_w$ 27.4 kDa, measured in THF relative to polystyrene standards; 50% glycolide) instead of RG 752 H. The particle concentration of the suspension was not sufficient to carry out a DLS measurement of the particle size distribution.

Only a few particles could be found in the produced suspension by SEM analysis. The size of the particles ranged from 200 nm to 400 nm. The yield of particles that were obtained by the process and collected in the container was 0.1 wt.-% relative to the applied amount of polymer.

The invention claimed is:

1. A process for preparing poly(lactide-co-glycolide) copolymer particles with an average particle size in the range of 50-800 nm, the process comprising:
   a) transferring ethanol and a poly(lactide-co-glycolide) copolymer with a content of polymerized monomer units of 55-80 mol % lactide and 20 to 45 mol % of glycolide and a molecular weight $M_w$ of 1,000-25,000 into a first reactor with a stirring equipment,
   b) feeding carbon dioxide into the first reactor so that carbon dioxide is from 65 to 85% by weight and the ethanol is 15 to 35% by weight whereby carbon dioxide and ethanol add up to 100%,
   c) mixing the poly(lactide-co-glycolide) copolymer, the ethanol, and the carbon dioxide by stirring and adjusting or maintaining the mixture in the first reactor to a temperature of at least 31 and up to 70° C. and a pressure of from 7.38 MPa to 50 MPa, where carbon dioxide enters the supercritical stage with ethanol as a co-solvent,
   d) stirring the mixture from c) for 1 to 5 hours, whereby at least a part of the poly(glycolide-co-lactide) copolymer becomes dissolved in the mixture of carbon dioxide and ethanol,
   e) transferring the mixture from d) into a second reactor under rapid reduction of the pressure and expansion with phase separation into a gas phase, an ethanol aerosol and an ethanolic suspension containing poly(lactide-co-glycolide) copolymer particles,
   f) removing the carbon dioxide gas and the ethanol aerosol from the second reactor, and
   g) obtaining the poly(glycolide-co-lactide) copolymer particles with an average particle size in the range of 50-800 nm in the form of an ethanolic suspension or in dry form from the second reactor.

2. The process according to claim 1, wherein a polydispersity-index (PI) of the poly(lactide-co-glycolide) copolymer particles obtained in g) is 0.2 or less.

3. The process according to claim 1, wherein the poly(lactide-co-glycolide) copolymer particles are obtained from the ethanolic suspension from step g) in dry form by evaporation of the ethanol.

4. The process according to claim 3, wherein the evaporation of the ethanol is performed by spray drying.

5. The process according to claim 1, wherein a yield of particles that were obtained in g) is at least 6% by weight % relative to the applied amount of poly(lactide-co-glycolide) copolymer in a).

6. The process according to claim 1, wherein the process is performed in a semi-continuous manner wherein a part of the poly(lactide-co-glycolide) copolymer becomes dissolved in d), and, simultaneous to the transfer of the mixture from d) into the second reactor in e), a mixture of ethanol and carbon dioxide in supercritical stage is added to the first reactor, so that a part or all of the undissolved poly(lactide-co-glycolide) copolymer becomes dissolved.

7. The process according to claim 6, wherein the addition of the mixture of ethanol and carbon dioxide in supercritical stage to the first reactor and the simultaneous transfer of the mixture from d) into the second reactor in e) is continued until the poly(lactide-co-glycolide) copolymer was dissolved to an amount of at least 98% and discharged to the second reactor in e) followed by f) and g).

8. The process according to claim 1, wherein the process is performed in a continuous manner by continuously:
   adding the poly(lactide-co-glycolide) copolymer, the carbon dioxide in supercritical stage, and the ethanol into the first reactor,
   transferring the mixture into the second reactor and removing carbon dioxide and ethanol, and
   obtaining the poly(lactide-co-glycolide) copolymer particles in ethanolic suspension.

9. The process according to claim 1, wherein the poly(lactide-co-glycolide) copolymer particles obtained from g) show a storage stability of at least two months in respect to constant particle size and absence of aggregation.

10. The process according to claim 1, wherein an active pharmaceutical ingredient is added in a).

11. The process according to claim 1, wherein poly(lactide-co-glycolide) copolymer particles comprised in the gas phase and/or the ethanolic aerosol which is removed from the second reactor in f) are obtained by a separation technique.

12. The process according to claim 11, wherein the poly(lactide-co-glycolide) copolymer particles are separated with an aero cyclone with electrostatical recirculation system.

13. A device for carrying out a process according to claim 1, the device comprising:
   a first reactor and a second reactor,
   an apparatus operable for mixing, cooling, heating, and pressuring carbon dioxide and ethanol and feeding the same into the first reactor, and
   an apparatus operable for transferring the mixture of carbon dioxide, ethanol, and poly(lactide-co-glycolide) copolymer particles into the second reactor, wherein the second reactor comprises outlets for the gas flow, outlets for the liquid flow, and a bottom plate.

14. The device according to claim 13, wherein the bottom plate is a double sheeted bottom plate with an upper sheet and a lower sheet, where the upper sheet is optionally in contact with the wall of the second reactor.

15. The device according to claim 13, wherein the device further comprises an aero cyclone, and
   wherein the aero cyclone is placed down-stream behind the second reactor so that the gas flow from the second reactor can be fed into the aero cyclone.

16. A device for carrying out a process according to claim 1, the device comprising:
   a first reactor and a second reactor,
   an apparatus operable for mixing, cooling, heating, and pressuring carbon dioxide and ethanol and feeding the same into the first reactor, and
   an apparatus operable for transferring the mixture of carbon dioxide, ethanol and poly(lactide-co-glycolide) copolymer particles into the second reactor, wherein the second reactor is an aero cyclone.

* * * * *